US008590428B2

(12) United States Patent
Ahlberg et al.

(10) Patent No.: US 8,590,428 B2
(45) Date of Patent: Nov. 26, 2013

(54) MULTIPLE-ANGLE SCISSOR BLADE

(75) Inventors: Russell E. Ahlberg, Rancho Santa Margarita, CA (US); Gary M. Johnson, Mission Viejo, CA (US); David T. Okihisa, Irvine, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 666 days.

(21) Appl. No.: 12/552,262

(22) Filed: Sep. 1, 2009

(65) Prior Publication Data

US 2010/0005929 A1    Jan. 14, 2010

Related U.S. Application Data

(63) Continuation of application No. 10/976,505, filed on Oct. 29, 2004, now abandoned.

(60) Provisional application No. 60/517,729, filed on Nov. 5, 2003.

(51) Int. Cl.
  *B21K 11/06* (2006.01)
(52) U.S. Cl.
  USPC .......................................................... 76/106.5
(58) Field of Classification Search
  USPC ................... 76/101.1, 104.1, 106.5; 606/174
  See application file for complete search history.

(56) References Cited

U.S. PATENT DOCUMENTS

| | | | |
|---|---|---|---|
| 2,086,121 A * | 7/1937 | De Bats ........................ | 76/104.1 |
| 2,708,311 A | 5/1955 | McCloud | |
| 4,279,076 A | 7/1981 | Jackson | |
| 4,392,658 A | 7/1983 | Redmond et al. | |
| 4,490,600 A * | 12/1984 | Rae ............................. | 219/69.12 |
| 4,794,684 A | 1/1989 | Vanlauwe | |
| 4,924,572 A * | 5/1990 | Vogel et al. ..................... | 30/253 |
| 5,172,479 A | 12/1992 | Keeton | |
| 5,396,900 A | 3/1995 | Slater et al. | |

(Continued)

FOREIGN PATENT DOCUMENTS

| | | |
|---|---|---|
| DE | 198 11 033 | 8/1999 |
| EP | 1 066 798 | 1/2001 |
| JP | 60 108260 | 6/1985 |
| JP | 2002 346248 | 12/2002 |

OTHER PUBLICATIONS

U.S. Appl. No. 11/334,027, filed Jan. 18, 2006. Title: Disposable Laparoscopic Instrument.
Co-Pending U.S. Appl. No. 11/059,806, filed Feb. 17, 2005. Title: System and Method for Actuating a Laparoscopic Surgical Instrument.
Co-Pending U.S. Appl. No. 11/735,798, filed Apr. 16, 2007. Title: Laparoscopic Scissor Blade.

(Continued)

*Primary Examiner* — Robert Scruggs
(74) *Attorney, Agent, or Firm* — John F. Heal

(57) ABSTRACT

A laparoscopic scissors, comprising a pair of blades connected at a pivot, each of the blades having a length, a tip portion, a body portion, an outer surface, an inner surface and a cutting edge is provided. The tip portion may have a first body thickness and the body portion may have a second body thickness different from the first body thickness. During the cutting operation, the blades progressively move over each other to provide a point contact along the cutting edges. In another aspect of the invention, a process of manufacturing the pair of scissors of the invention is disclosed, comprising the steps of forming the blades into a desired shape with wire EDM processes from a pre-hardened block of material, and sharpening the cutting edges of the blades.

19 Claims, 3 Drawing Sheets

(56) References Cited

U.S. PATENT DOCUMENTS

| | | | |
|---|---|---|---|
| 5,431,071 | A | 7/1995 | Williams |
| 5,584,845 | A | 12/1996 | Hart |
| 5,769,849 | A * | 6/1998 | Eggers ............................ 606/48 |
| 6,168,605 | B1 | 1/2001 | Measamer et al. |
| 6,493,943 | B1 * | 12/2002 | Linden ............................ 30/252 |
| 6,612,204 | B1 | 9/2003 | Droese et al. |
| 6,749,609 | B1 | 6/2004 | Lunsford et al. |
| 2002/0083598 | A1 * | 7/2002 | Julien ............................ 30/350 |
| 2003/0019332 | A1 | 1/2003 | Korb et al. |

OTHER PUBLICATIONS

Co-Pending U.S. Appl. No. 11/345,964, filed Feb. 2, 2006. Title: Surgical Instrument With Removable Shaft Apparatus and Method.

Intl. Search Report and Written Opinion, for Intl. Patent Application No. PCT/ 04/36024, mailed Jan. 17, 2006, 7 pages.

U.S. Appl. No. 10/976,505, filed Oct. 29, 2004, Title: Multliple Scissor Blade.

European Patent Office, Supplementary European Search Report for European Application No. EP 04 79 6765 entitled "Multiple Angle Scissor Blade" dated Mar. 3, 2011.

* cited by examiner

MULTIPLE-ANGLE SCISSOR BLADE

This application is a continuation of currently-pending U.S. patent application Ser. No. 10/976,505, filed on Oct. 29, 2004, entitled "Multiple-Angle Scissor Blade," which is a non-provisional application claiming the priority of provisional application Ser. No. 60/517,729, filed on Nov. 5, 2003, entitled "Multiple-Angle Scissor Blade," both of which are fully incorporated herein by reference.

BACKGROUND OF THE INVENTION

1. Field of the Invention

This invention generally relates to laparoscopic scissors and, more particular, to laparoscopic scissors having multiple cutting angles and multiple thicknesses.

2. Discussion of Related Art

During surgery, surgeons will typically need to cut into a multitude of objects such as tissues, suture and metal staples. A goal in the design of scissors and, in particular, in the design of scissors' blades is to optimize its effectiveness in cutting through different objects. For cutting through soft tissues, a large angle ground into the blade is most effective. That is, when sharp edges shear against each other, any tissue which comes between the blades of the scissors will get cut. The large angle on each blade is effective when cutting soft material because the blades can stay thin and razor sharp throughout the cut. A thin and sharp edge is optimal for soft materials because there is less resistance throughout the cut.

In contrast, when cutting through something hard such as a metal staple, the fine edge of a typical scissors' blade may not be as effective as when cutting soft tissue. A very fine and sharp edge may deform when required to cut a hard object. That is, a blade having a very large angle ground into it will deform if used to cut hard objects. To prevent the blades from deforming, the blades have to be designed to be thicker at and behind the point of cutting so that the blade edges do not deform. Having a small angle on the cutting edge of a scissor blade like this would help when cutting through hard materials such as staples or hard objects. Accordingly, because tissue and staples are typically cut with the same instrument, there is a need in the art for a laparoscopic scissors having both a large angle cutting edge and a small angle cutting edge on the same device.

SUMMARY OF THE INVENTION

The invention is directed to a pair of laparoscopic scissors, comprising a pair of blades connected at a pivot, each of the blades having a length, a tip portion, a body portion, an outer surface, an inner surface and a cutting edge, the cutting edge forming an angle with the outer surface along the length of the blade such that tension during a cutting operation at the tip portion is about the same as tension at the body portion during the cutting operation. In one aspect of the invention, the angle formed is continuously changing over the length of the blade. In another aspect, the angle at the tip portion is greater than at the body portion, and the angle progressively decreases from the tip portion to the body portion. The tip portion may have a first body thickness and the body portion may have a second body thickness different from the first body thickness. In yet another aspect, the blade may comprise a proximal portion proximal to the body portion having a third body thickness, wherein the second body thickness is thicker than the first and third body thicknesses.

The cutting operation may include cutting at least one of a body tissue, a suture and a surgical staple. During the cutting operation, the blades progressively move over each other to provide a point contact along the cutting edges. It is appreciated that the blades may be thickened in a number of locations and combinations including: (1) one blade could be thicker than the other to force the opposing blade to flex; (2) both blades could be thicker at the body or throat sections to give more strength when cutting staples; (3) each blade could be thickened on one side or the other to stiffen certain locations; and (4) the tips of each blade could be thicker than the body or throat sections to provide increased tension at the tips.

In another aspect of the invention, a process of manufacturing the pair of scissors of the invention is disclosed, comprising the steps of form grinding the blades into a desired shape from a pre-hardened block of material, and sharpening the cutting edges of the blades. It is appreciated that the blades of the invention may also be formed through other processes including Wire EDM (Electrical Discharge Machining), laser cutting, waterjet cutting, machining, cast or metal injection molding, and other independent profile manufacturing process. The manufacturing process of the invention is beneficial in that each profile can be accurately controlled, and the parts will be exact every time. Additionally, there is no heat-treating step afterwards because it was done prior to grinding and cutting. Another feature of the manufacturing process of the invention is that the parts can be made with any number of multiple thickness sections in the profile.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features, advantages and principles of the invention. In the drawings.

DESCRIPTION OF THE INVENTION

The following description refers to the accompanying drawings that illustrate the embodiments of the invention. Other embodiments are possible and modifications may be made to the embodiments without departing from the spirit and scope of the invention. Thus, the following description is not meant to limit the invention.

Figure 1:
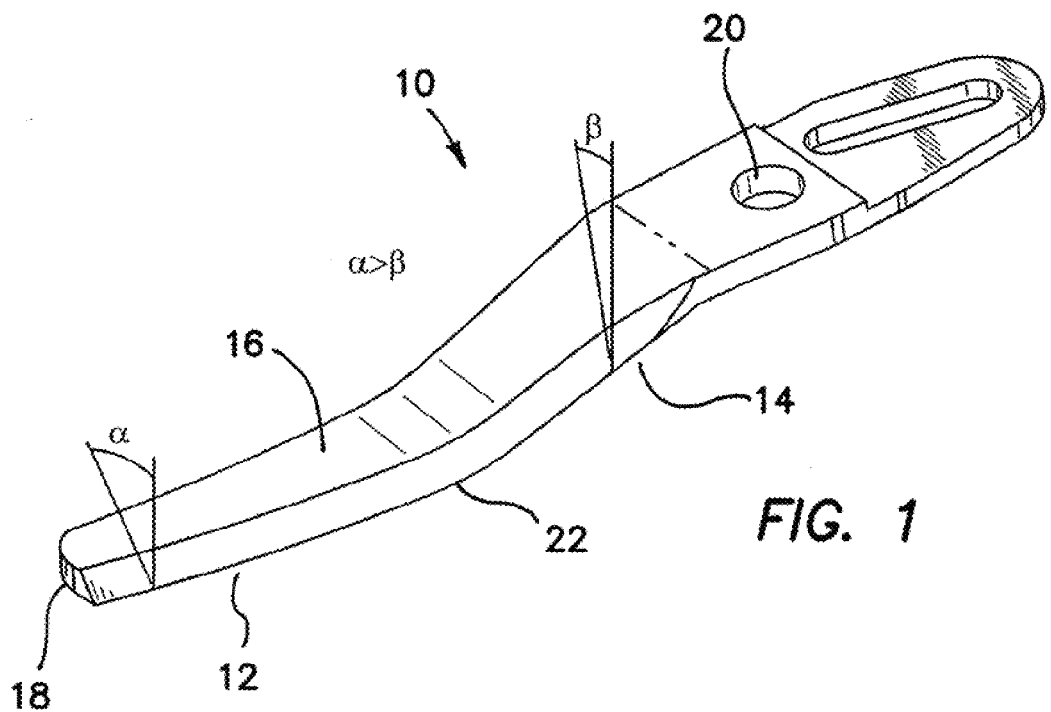
FIG. 1 illustrates a multiple-angle scissor blade in accordance with a first embodiment of the invention where the angle is continuously changing.

Referring now to the drawings, and in particular to FIG. 1, there is shown an exemplary blade 10 of a scissors in accordance with the first embodiment of the invention. The blade 10 includes a tip portion 12, a body or throat portion 14, an outer surface 16, an inner surface 18, a cutting edge 22 and a pivot area 20. The cutting edge 22 forms an angle with the outer surface 16 along the length of the blade 10 such that tension at the tip portion 12 is about the same as tension at the body or throat portion 14. The function and effectiveness of the scissor blades depend heavily on the tension and angle the cutting surfaces are to each other. The blades are designed such that the tension when cutting is about the same throughout the length of the blades, e.g., at the tip and at the body or throat portion. In contrast, the conventional scissors have uniform blade thicknesses where tension at the tip is less than tension at the body portion because it is further away from the pivot. As a result, the conventional scissors blades may deform when cutting through harder and denser objects.

Figure 6:
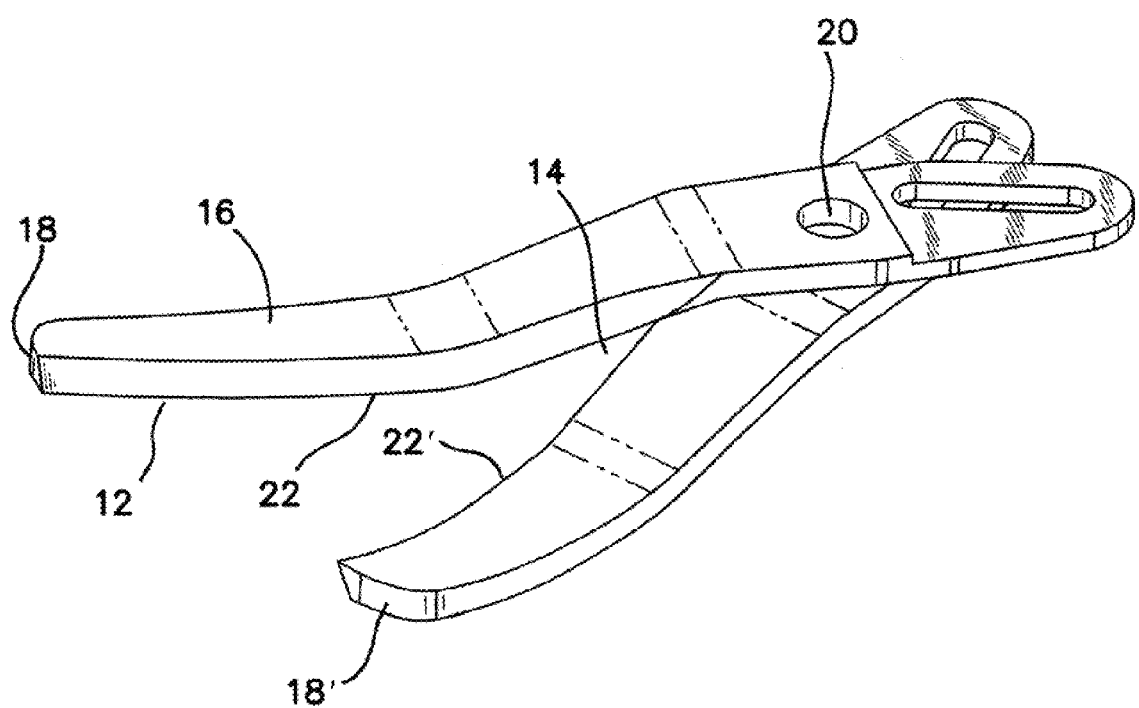
FIG. 6 shows pair of scissors and illustrating the cutting edges and throat portion in accordance with an embodiment of the invention.

A novel feature of the invention is that an angle a formed between the cutting edge 22 and the outer surface 16 at the tip portion 12 is different from an angle β formed between the cutting edge 22 and the outer surface 16 at the body or throat portion 14. That is, the angle formed between the cutting edge 22 and the outer surface 16 may be continuously changing over the length of the blade 10. In one aspect, the angle α is greater than the angle β. With this aspect, the edge of the blade would start at a very large angle α at the tip portion 12 and as it proceeds back along the edge toward the back of the blade, the angle starts to reduce until it is much smaller at the body or throat portion 14 of the blade. An advantage of the multiple-angle scissor blade 10 of the invention is the angles that most effectively cut different materials are all included on the same blade. Surgeons typically "snip" at tissue with the tip of the blades. Thus, grinding a large angle edge near the tip portion 12 of blade 10 would be most effective. Surgeons typically cut suture, which is a little harder than tissue, somewhere in the middle of the blades. Thus, grinding a smaller angle near the mid-portion of blade 10 would be optimal for suture. When cutting through very hard staples, surgeons will typically take a bite and force the staple somewhere between the center and the throat of the blades as illustrated in FIG. 6. Thus, grinding a very small angle into the blade near the throat portion 14 would be optimal for cutting hard materials. Also, the most leverage is available at the throat section, making the cut easier.

It is further appreciated that the blades may be of any shape. In one aspect, the blades define a slight curve towards one another, which provides sharper cutting due to a single point cutting action. The tip portion 12 may also be provided by an outer edge 26. The tapered tip portion 12 allows insertion of the scissor blades into a cavity in the body of a patient. Additionally, the tip is rounded at its outer edge 26 to avoid inadvertent puncturing or abrasion by the tip during use.

Figure 2:
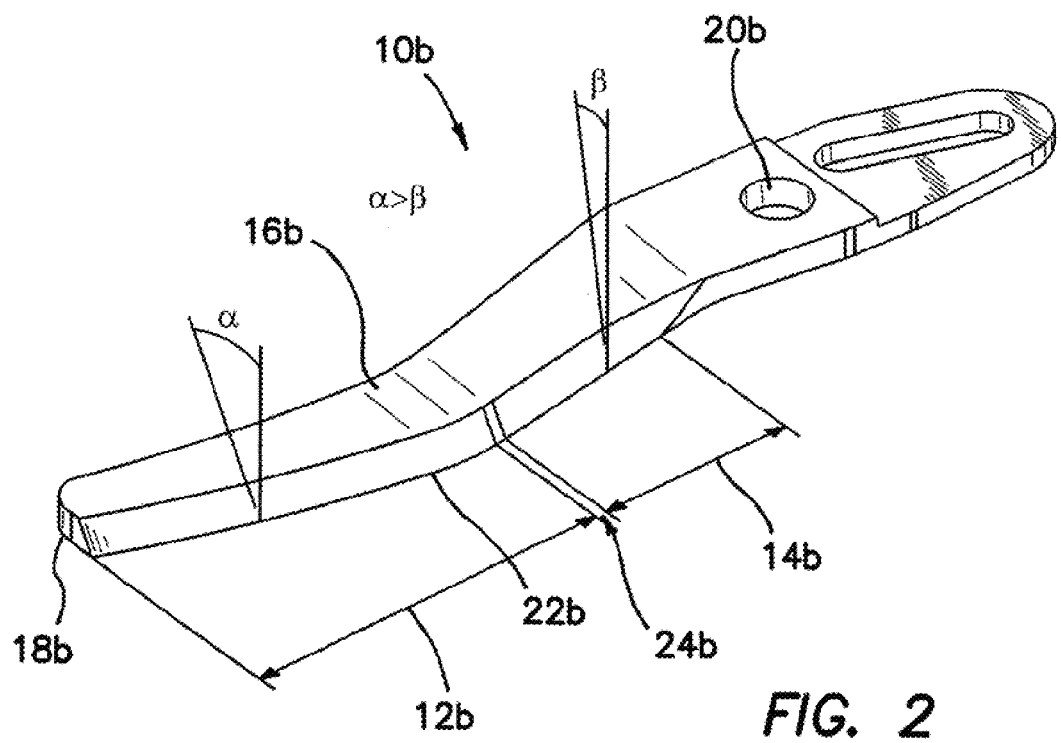
FIG. 2 illustrates a multiple-angle scissor blade in accordance with another embodiment of the invention where an angle is held constant in each section of the blade.

In another embodiment of the invention as illustrated in FIG. 2, multiple sections of different angles may be grinded in the blade 10b of the scissors. For example, the cutting edge 22b of the blade 10b may start out forming a very large angle α with the outer surface 16b at the tip portion 12b. This angle α could be held constant for a given length. The angle α could then transition into a smaller angle β, which then could be held constant for a next given length. There could be as many sections along the blade as desired to obtain the various angles needed. For example, the angle α may be held constant over the tip portion 12b and the angle β may be held constant over the throat portion 14b with an angle transition portion 24b formed between the tip portion 12b and the throat portion 14b as illustrated in FIG. 2.

Figure 3:
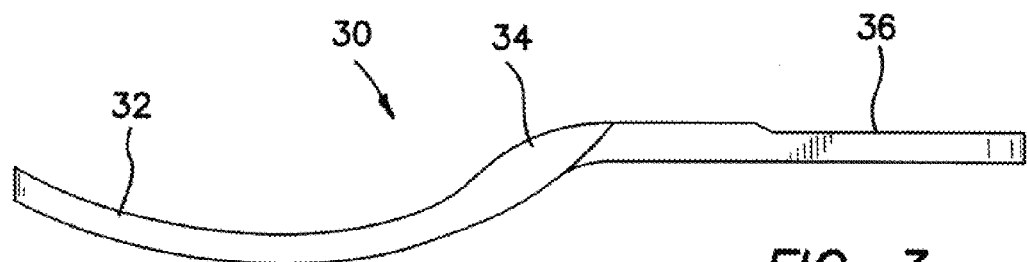
FIG. 3 illustrates a side view of a blade having multiple thicknesses in accordance with another embodiment of the invention.

Another method for keeping the tension tight at the tips of the blades is to vary the thicknesses of the scissors blades. Referring to FIG. 3, there is shown a side view of a blade 30 having a tip portion 32, a mid-portion 34 and proximal portion 36. In this embodiment of the invention, the mid-portion 34 is thicker than the tip portion 32 and the proximal portion 36. That is, when the blades slide over each other during a cutting stroke, the blades flex so that only one point is actually touching. This flexure and the tension between the blades can be controlled and "forced" to different areas by varying the thickness of the blades. By providing a scissors with the blades having multiple thicknesses, the tension of each blade can be controlled and the flexure can be forced into certain areas on the blade. A thicker blade is also stronger in that section. When cutting through hard materials such as staples, a thicker, stronger blade is always beneficial.

It is appreciated that the scissors blades can be thickened in a number of locations and combinations such as:

(1) One blade could be thicker than the other to force the opposing blade to flex;

(2) Both blades could be thicker at the throat section to give more strength when cutting staples;

(3) Individual blades could be thickened on one side or the other to stiffen certain locations; and (4) The tips of the blades could be thicker than the throat section to provide increased tension at the tips.

In another aspect of the invention, it is appreciated that the scissors can be manufactured in a number of different ways. The most common method is to stamp and form the blades from a predetermined thick material, and then grind a razor edge into them. This method is relatively inexpensive, but if the blades need to be heat treated after forming, the parts can twist and distort thereby reducing or eliminating the tension between the blades. Thus, another process may be required to bring the parts back into specification so the proper blade tension may be realized.

Since the blade tension is the most critical aspect of a scissors, it needs to be controlled from the beginning. A block of material that is heat treated to the required hardness can be manufactured prior to manufacturing the blades. A form-grinding machine can grind one profile into the blade such as the cutting profile 40 illustrated in FIG. 4. Form grinding is the process of taking a diamond impregnated grinding stone that has a particular shape cut into it, and shaving away the pre-hardened material until a block has the desired profile.

Figure 4:
FIG. 4 illustrates a profile of a blade formed from grinding in accordance with a manufacturing process of the invention.
Figure 5:
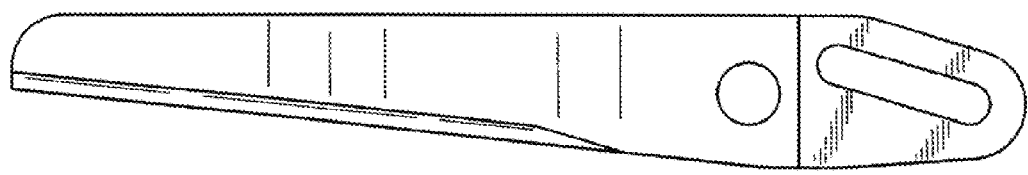
FIG. 5 illustrates a top view of a blade formed from another independent profile manufacturing process in accordance with an embodiment of the invention.

The profile as shown in FIG. 4 is not limited to grinding and may be cut with Wire EDM (Electrical Discharge Machining). Wire EDM is a metal removal technique using a controlled electrical current or spark erosion. The EDM machine moves a wire through the part eroding material away. With Wire EDM, there is always a gap between the part and the wire so there is no contact and virtually no deflecting force applied to the part, which ensures greater accuracy and tight tolerances of the finished part. The parts can also be formed by machining, cast injection molding or metal injection molding. The molded or cast part or block can then be further processed by EDM, laser cutting, waterjet cutting, or other manufacturing process to produce the finished parts. Waterjet cutting is a process of directing a fine, very high-pressure water stream to a material to cut or form a part. The waterjet stream may include fine metal particles to facilitate cutting. With the process of the invention, the profile can be accurately controlled, and the parts can be accurately produced every time. Additionally, there is no heat-treating step afterwards because it was done prior to grinding and cutting. The final step would be the edge sharpening. Another advantage of the independent profile manufacturing process is that the parts can be made with any number of multiple thickness sections in either profile as illustrated in FIG. 3. To do this with a traditional stamping process would be difficult as well as expensive, if possible at all.

Many alterations and modifications may be made by those having ordinary skill in the art without departing from the spirit and scope of the invention. Therefore, it must be understood that the illustrated embodiments may have been set forth only for the purposes of examples and that they should not be taken as limiting the invention.

The invention claimed is:

1. A process of manufacturing a pair of surgical scissors having a pair of blades connected at a pivot, each of the blades having a length, a tip portion, a body portion, an outer surface, an inner surface and a cutting edge, the cutting edge forming an angle with the outer surface along the length of the blade, comprising the steps of:
heat treating a block of material to form a pre-hardened block of material having a desired hardness;
applying an electrical discharge machining process to the pre-hardened block of material to accurately form the blades into a desired blade profile comprising the inner surface and the outer surface of the blade from the pre-hardened block of material;
refraining from additional heat treating of the blades having the desired blade profile formed by the electrical discharge machining process; and
sharpening the cutting edges of the blades.

2. The process of claim 1, wherein the electrical discharge machining process comprises a wire electrical discharge machining process using controlled electrical current erosion.

3. The process of claim 1, wherein the electrical discharge machining process comprises a wire electrical discharge machining process using spark erosion.

4. The process of claim 1, wherein the angle formed is continuously changing over the length of the blade.

5. The process of claim 1, wherein the angle at the tip portion is greater than at the body portion.

6. The process of claim 5, wherein the angle progressively decreases from the tip portion to the body portion.

7. The process of claim 1, wherein the blade profile comprises a variable blade thickness from the tip portion to the body portion of the blade.

8. The process of claim 7, wherein the blade profile comprises a relatively thick section adjacent the body portion and a relatively thin section at the tip portion.

9. The process of claim 1, wherein the blade profile defines a blade comprising a curve.

10. The process of claim 1, wherein applying an electrical discharge machining process to accurately form the blades into a desired blade profile comprises accurately forming the blades into a desired blade profile having a desired blade tension without an additional tension-correcting process.

11. The process of claim 1, wherein the tip portion comprises a rounded outer edge.

12. The process of claim 1, wherein both blades of the pair of blades are formed from the block of pre-hardened material.

13. A process of manufacturing a pair of surgical scissors having a pair of blades connected at a pivot, each of the blades having a length, a tip portion, a mid portion, and a proximal portion opposite the tip portion, an outer surface, an inner surface and a cutting edge, the cutting edge forming an angle with the outer surface along the length of the blade, comprising the steps of:
heat treating a block of material to form a pre-hardened block of material having a desired hardness;
applying an electrical discharge machining process to the pre-hardened block of material to accurately form the blades into a desired blade profile comprising the inner surface and the outer surface of the blade from the pre-hardened block of material, the desired blade profile defining a desirable blade tension at the cutting edge without additional correcting processes;
sharpening the cutting edges of the blades; and
connecting the blades at the pivot.

14. The process of claim 13, wherein the electrical discharge machining process comprises a wire electrical discharge machining process.

15. The process of claim 13, wherein sharpening the cutting edges of the blades comprises grinding the cutting edges of the blades.

16. The process of claim 13, wherein the desired blade profile comprises a variable thickness blade.

17. The process of claim 16, wherein the variable thickness blade comprises a relatively large thickness at the mid portions of the blades and relatively smaller thicknesses at the tip portions and the proximal portions of the blades.

18. The process of claim 13, wherein the angle varies over the length of the cutting edge.

19. The process of claim 13, wherein the desirable blade tension is a tension when cutting that is approximately constant along the length of the blade.

* * * * *